United States Patent [19]

Anderson et al.

[11] Patent Number: 4,558,007

[45] Date of Patent: Dec. 10, 1985

[54] PROCESS FOR DETECTING LDH$_k$ ISOZYME ACTIVITY IN HUMAN SERUM FOR USE AS A DIAGNOSTIC AID AND FOR MONITORING RESPONSE TO CANCER THERAPY

[75] Inventors: Garth R. Anderson, South Wales; Kenneth F. Manly; Arnold Mittelman, both of Buffalo, all of N.Y.

[73] Assignee: Health Research, Inc. (Roswell Park Divison), Buffalo, N.Y.

[21] Appl. No.: 505,190

[22] Filed: Jun. 17, 1983

[51] Int. Cl.$^4$ .................................................. C12Q 1/32
[52] U.S. Cl. ......................................................... 435/26
[58] Field of Search .......................................... 435/26

[56] References Cited

U.S. PATENT DOCUMENTS 4,258,131  3/1981  Takagahara et al. ................. 435/26

OTHER PUBLICATIONS

Anderson et al., LDH$_k$, a Uniquely Regulated Cryptic Lactate Dehydrogenase Associated with Transformation by the Kirsten Sarcoma Virus, J. of Bio. Chem., vol. 256, No. 20, pp. 10583–10591 (Oct., 1981).

Anderson et al., LDH$_k$, An Unusual Oxygen-Sensitive Lactate Dehydrogenase Expressed in Human Cancer, Proc. Natl. Acad., Sci. USA, vol. 78, No. 5, pp. 3209–3213 (May, 1981).

Dietz et al., Separation and Quantitation of Lactic Dehydrogenase Isoenzymes by Disc Electrophoresis, Analytical Biochemistry 20, 246–257 (1967).

*Primary Examiner*—Sam Rosen
*Attorney, Agent, or Firm*—Christel, Bean & Linihan

[57] ABSTRACT

An improved assay procedure for quantitatively detecting LDH$_k$ isozyme in human serum is provided which utilizes previously known electrophoretic gel separation procedures combined with an improved staining method wherein the staining solution has a constant temperature of about 37° C. and a pH of about 8.0, and is contacted with the gel matrix for at least 3 hours in the absence of oxygen and light. This improved assay procedure may be used as an adjunct to other procedures for diagnosing the presence of primary cancer, as a post-operative indicator of metastatic cancer and in monitoring the success of cancer therapy.

15 Claims, 5 Drawing Figures

PROCESS FOR DETECTING LDH$_k$ ISOZYME ACTIVITY IN HUMAN SERUM FOR USE AS A DIAGNOSTIC AID AND FOR MONITORING RESPONSE TO CANCER THERAPY

The invention described herein was made in the course of work under the research grant CA32022 from the National institutes of Health and a grant from the Sklarow Foundation.

BACKGROUND OF THE INVENTION

This invention relates to an improved process for detecting a specific isozyme of lactate dehydrogenase, termed LDH$_k$ in the serum of cancer patients. More particularly, this invention relates to an improved assay for quantitatively determining the level of LDH$_k$ in human serum, to aid in diagnosing the presence of cancer and to monitor the success of cancer therapy.

The enzyme lactate dehydrogenase (LDH; L-lactate: NAD+oxidoreductase) catalyzes the reaction:

Pyruvate+NADH$_2$⇌Lactate+NAD

Lactate dehydrogenase has a number of isozymes; isozymes are enzymes possessing the same or a similar catalytic function, but are distinguishable by either biochemical, physical or immunological means. The first isozymes of lactate dehydrogenase were found to be tetramers composed of two distinct polypeptide parent chains termed H (heart) and M (muscle), named for the organs from which they are readily obtained. The H and M subunits combine to give rise to the five classical isozymes of LDH. The five tetrameric isozymes of LDH are: H$_4$, H$_3$M, H$_2$M$_2$, HM$_3$ and M$_4$. At pH 7, H$_4$ is the most negatively charged and thus appears nearest the anode after zone electrophoresis, while M$_4$ appears nearest the cathode. H$_4$ functions predominantly in the aerobic oxidation of lactate and is found in high concentration in heart muscle, erythrocytes, and the renal cortex. M$_4$ is primarily involved in the reduction of pyruvate and anaerobic metabolism, and is found in highest concentrations in skeletal muscle, liver, skin and the ileum.

Another isozyme, termed X$_4$, has been isolated from spermatozoa and testis, and is a tetramer composed of another subunit form of LDH, referred to as the X subunit. This subunit is encoded by a third gene separate from those encoding the synthesis of the H and M subunits. This, along with the fact that the other five isozymes have been electrophoretically resolved into numerous subbands, suggests that the molecular nature of lactate dehydrogenase is complex.

In 1981, another isozyme of LDH was characterized in cells transformed by the Kirsten murine sarcoma virus (KiMSV). This unique isozyme was designated LDH$_k$. It has been isolated in anaerobically stressed rat cells and in Kirsten sarcoma virus-infected non-rat cells. LDH$_k$ purified from cells transformed by a temperature-sensitive transforming gene mutant of KiMSV was thermolabile relative to LDH$_k$ purified from cells infected by wild type virus. Therefore, it is thought to actually be encoded by KiMSV, and most likely by its transforming gene. [Anderson, G. R. et al., J. Biol. Chem. 256: 10583–10591 (1981)].

LDH$_k$ is readily distinguishable from the other known isozymes of LDH. Specifically, it is essentially inactive if assayed under a normal atmosphere due to inhibition by oxygen, has subunits of 35,000 and 22,000 daltons (which appear to cleave from a 57,000—dalton precursor), is more basic than other LDH isozymes and is inhibited by guanosine triphosphate (GTP) and more strongly by the related compounds 5',5' diadenosine tetraphosphate (AP$_4$A) and 5',5' diguanosine tetraphosphate (Gp4G).

The discovery that human tumors contain high levels of LDH$_k$ activity was first reported in 1981 [Anderson, G. R. et al., Proc. Nat. Acad. Sci. USA 78: 3209–3213, 1981]. In this study, 16 different human carcinomas were analyzed for the presence of LDH$_k$, and 11 out out of the 16 tumor tissues tested showed a 10 to 500-fold increase over the LDH$_k$ activity seen in adjoining non-tumor tissues. In contrast, other LDH isozymes exhibited only a 2 to 5-fold increase in the tumor tissues as compared with nontumor tissue. These researchers analyzed tumor tissues from human colon, mammary, laryngeal, renal, parotid and stomach carcinomas, and malignant melanoma. The LDH$_k$ detected in these human tumor tissues was inactive in the presence of oxygen, being activated by the presence of nitrogen or in the presence of cyanide, and was inhibited by GTP. These results suggested that LDH$_k$ might be clinically useful as a diagnostic tumor marker, particularly if it were released outside the tumor tissue.

At the present time there are several biochemical substances known to be secreted by tumor cells and released outside the tumor, which are sufficiently different in quantity or quality from products of normal cells to act as "tumor markers". One such marker is carcinoembryonic antigen (CEA) which is utilized to detect adenocarcinomas of the digestive system, particularly carcinoma of the colon. A very sensitive radioimmunoassay has been developed to detect small amounts of CEA in the blood which assay procedure has proven to be valuable in the early diagnosis of colon carcinoma and in detecting its recurrence after surgery.

A clinical spectrophotometric assay for LDH activity is presently utilized for monitoring myocardial, liver and hematologic disorders. Numerous studies have been done to investigate alterations in serum levels of the classical isozymes of LDH in human cancer, and assays of the classical isozymes of LDH in human tumor tissues have also been done. A definite and consistent shift in the pattern of molecular forms of LDH has been found in a series of malignant human neoplasms as compared with benign tumors and normal controls. Although evidence has been found for an increase in total LDH activity in malignant tumors, metastatic nodules have been shown to have lower LDH activity levels and different LDH compositions when compared with their associated primary tumors. Accordingly, due to the irregular patterns of expression of the classical LDH isozymes in human cancer serum, assay for these isozymes is not presently used as an aid in detecting or monitoring the progression of malignant diseases. It should be noted that since LDH$_k$ is inactive when assayed in the presence of oxygen, it would not have been detected in any of the previous studies.

Preliminary unpublished data showed that LDH$_k$ is released into the serum of cancer patients. Therefore, it was thought that a quantitative assay procedure for the expression of LDH activity in human serum might be useful in the clinical realm. However, conventional clinical assaying techniques have not been sufficiently sensitive to permit a meaningful quantitative determination of LDH$_k$ activity in human serum.

SUMMARY OF THE INVENTION

In accordance with the present invention an improved assay procedure for quantitatively detecting $LDH_k$ in human serum is described which provides a sensitive means for distinguishing between normal individuals and those having cancer. The assay procedure disclosed herein may be used as an adjunct to other procedures for diagnosing the presence of primary cancer, as a post-operative indicator of metastatic cancer and in monitoring the success of cancer therapy. Specifically, the present inventive process utilizes a previously described electrophoretic gel separation procedure combined with an improved staining method wherein the staining solution or cocktail used to develop the gel matrix is maintained at a temperature of about 37° C. and at a pH of about 8 for at least three (3) hours in the absence of oxygen and light.

DETAILED DESCRIPTION OF THE INVENTION

Figure 1:
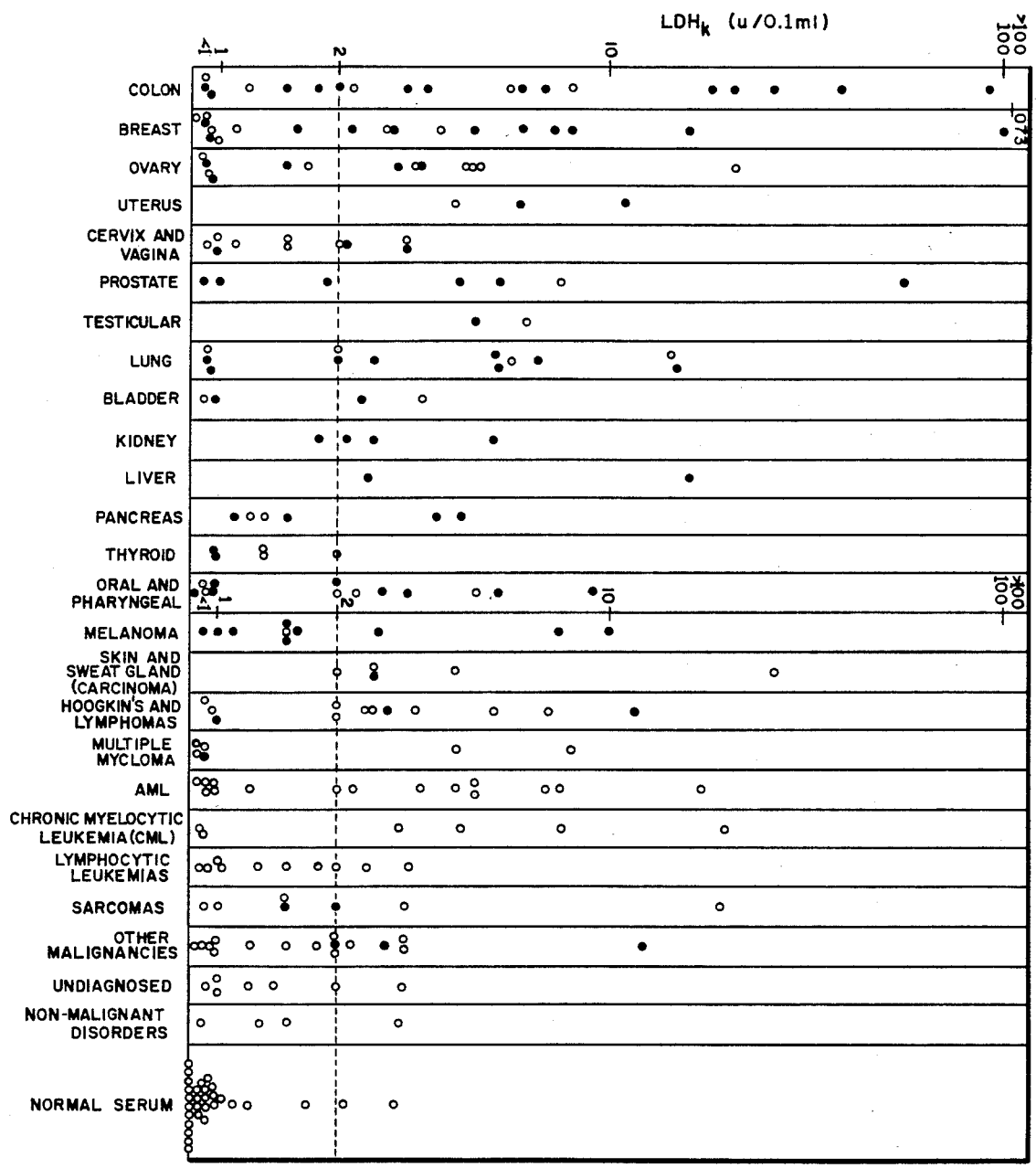
FIG. 1 shows the $LDH_k$ activity found in the serum of 206 cancer patients and 30 healthy donors.

In accordance with the present invention, an improved process for quantitatively determining the presence of $LDH_k$ in human serum has been developed. This process is based on a modification of the procedure used by Anderson, G. R. et al. as reported in Proc. Nat. Acad. Sci. USA 78 3209–3213 (1918), which disclosure is hereby incorporated by reference.

The above-cited publication was directed to the detection of $LDH_k$ in human tumor and nontumor tissue, and used reverse-polarity gels utilizing an imidazole/borate buffer system. $LDH_k$ has a positive charge at pH 8.9 and migrates toward the cathode. The gels used were 5.5% polyacrylamide photopolymerized with a riboflavin catalyst in the absence of persulfate. The gel contained 0.15M potassium borate, pH 8.3. The upper reservoir buffer was composed of 0.08M imidazole and 0.02M boric acid, pH 8.9. The lower reservoir buffer was 0.1M potassium borate, pH 8.3. Gels were run approximately 16 hours at a constant voltage 220 V. with samples migrating toward the cathode. Cooling was provided by circulating ice water. Other borate buffered separation compositions would have been feasible, however, the above described buffers were found to be most convenient for serum analysis.

At the completion of the run, gels were stained specifically for lactate dehydrogenase activity according to the nitroblue tetrazolium/phenazine methasulfate procedure of Dietz and Lubrano [Anal. Biochem. 20: 246–257 (1967)] wherein it was suggested that the gels be submerged in about 2.3 mls of a pH 7.4 staining solution and then incubated at 37° C. in an oxygen environment for no longer than two hours. However, in order to stain the $LDH_k$ isozyme the staining was performed under a nitrogen atmosphere and the staining mixture was supplemented with 2% glycerol to complex the borate. Gels were fixed with 45% methanol/10% acetic acid (vol/vol), then either photographed or scanned with a tungsten filament recording densitometer (Quick Scan Jr., Helena Laboratories), and $LDH_k$ activity was adequately detected in tumor and nontumorous tissue samples.

However, when this same staining technique was later applied in an attempt to detect $LDH_k$ in human serum in order to investigate the utility of serum $LDH_k$ as a cancer marker, positive results were obtained in only a few cases due to the extreme insensitivity of the prior staining technique.

The use of serum $LDH_k$ as a clinical marker requires an assay sensitive enough to detect it in most of those cases where it is expressed. Ideally, a satisfactory assay procedure would detect a base level of expression in all individuals, and define the degree of elevation in cancer patients. This type of assay was not possible using conventional staining procedures, since the enzymatic activity of serum $LDH_k$ has a threshold of about 1 gel unit and most normal individuals fall below this level in a range which would be undetectable with previously disclosed staining procedures.

However, it has now been discovered that $LDH_k$ levels can be detected and quantitatively expressed in nearly all cancer patients' serum when the staining procedure is modified so that the staining mixture used to develop the gel matrix immersed therein has a pH of about 8.0 and is maintained at a constant temperature of about 37° C. for at least 3 and preferably 4 or more hours in the absence of oxygen and light.

The preferred temeperature for the developing solution is 37° C. although suitable results can also be obtained from between about 30°–43° C. Maintaining this temperature throughout the development time of the gel matrix is critical to permit the $LDH_k$ isozyme to react with the lactate and $NAD^+$.

It is advantageous that the staining solution have a pH from between about 7.8–9.0 and preferably 8.0 to insure stain development. The recommended staining solution comprises the following ingredients:

2.0 g lithium lactate
140 mg $NAD^+$
2 ml (2.3 mg/ml) phenazine methasulfate (PZ)
2 ml (40 mg/ml) nitroblue tetrazolium (NBT)
4 ml glycerol
180 ml water ($H_2O$)

which solution is buffered to a pH of between 7.8–9.0 by the addition of 20 ml of a 1M Tris buffer having a pH of 8.0. Specific ingredients and amounts may vary over a wide range, but the above indicated ratio of the PZ to NBT should be maintained as is well known in the prior art.

To illustrate the effect of temperature, pH and time of reaction on the quantitative measurement of serum $LDH_k$ activity, assays were carried out wherein each factor was studied separately keeping other reaction conditions essentially constant. $LDH_k$ used in these studies was obtained from sources where it is more readily obtained: tissue culture cells transformed by the Kirsten sarcoma virus, rat muscle and retina. Findings obtained with enzyme from these sources were then verified as to their applicability to the human serum enzyme. This was not unreasonable, since $LDH_k$ from all sources has similar electrophoretic behavior, similar oxygen regulation and similar substrate dependence. The data collected is illustrated in the following Table:

TABLE 1
Initial Studies

I. Optimization of Assay Temperature:

| | $LDH_k$ Source | Assay Temperature | $LDH_k$ Activity |
|---|---|---|---|
| Experiment 1. | Kirsten virus transformed NRK cells | 25° | 0.1 |
| | | 29° | 0.2 |
| | | 33° | 4.4 |
| | | 37° | 5.3 |
| | | 41° | 5.5 |
| Experiment 2. | Kirsten virus transformed NRK | 20° | 3.4 |
| | | 30° | 9.4 |
| | | 37° | 16.1 |
| | | 43° | 10.3 |
| | | 46.5° | 8.4 |
| | | 51° | 1.2 |

II. Optimization of Assay pH:

| $LDH_k$ Source | Assay pH | $LDH_k$ (% of pH 8.0) |
|---|---|---|
| retina | 6.1 | 55 |
| | 7.0 | 72 |
| | 7.5 | 93 |
| | 8.0 | 100 |

III. Optimization of Assay Time:

| $LDH_k$ Source: | $LDH_k$ Activity after Assay Time (hours) | | | | |
| Human cancer patient sera | 0 | 2 | 4 | 6 | 8 |
|---|---|---|---|---|---|
| patient 177 | 0.0 | 0.0 | 7.8 | 7.8 | 12.2 |
| patient 189 | 0.0 | 0.0 | 0.6 | 0.6 | 1.2 |

(note published procedure used 2 hour assay time)

As may be readily seen from the data illustrated in Table 1, a detectable level of $LDH_k$ activity i.e. above 1.0 activity unit, was obtained in all cases when the temperature was 30° C. or higher. Below about 46.5° C. detectable activity levels fell sharply. In addition, optimal pH was demonstrated to be about 8.0. As illustrated by the bottom portion of the Table, no dectectable levels were produced when the assay (stain reaction time) was maintained for 2 hours or less. The preferred reaction time was between 4 and 8 hours although sufficient activity may be detected at about 3 hours.

The correlation of the data shown in Table 1 to $LDH_k$ levels detected in human serum was further demonstrated in Table 2 below:

TABLE 2

| Enzyme Source | Staining Solution Temperature | pH | $LDH_k$ Activity | Detectable Activity |
|---|---|---|---|---|
| Kirsten sarcoma virus transformed NRK | 20° | 7.5 | 3.4 | 0.21 |
| Kirsten sarcoma virus transformed NRK | 30° | 7.5 | 9.4 | 0.58 |
| Kirsten sarcoma virus transformed NRK | 37° | 7.5 | 16.1 | 1.00 |
| Human patient serum | 20° | 7.5 | 19.5 | 0.52 |
| Human patient serum | 37° | 7.5 | 37.5 | 1.00 |
| Human patient serum | 20° | 7.0 | 0 | 0.00 |
| Human patient serum | 20° | 7.5 | 4 | 0.22 |
| Human patient serum | 20° | 8.0 | 5 | 0.28 |
| Human patient serum | 37° | 8.0 | 18 | 1.00 |
| Human patient serum | 20° | 8.5 | 12 | 0.67 |
| Human patient serum | 37° | 8.5 | 13 | 0.72 |

Stain development must be carried out in the dark because PZ is light sensitive and undergoes a photodecomposition in the presence of light which causes an unwanted blackening of the gel matrix.

Also, it is critical that oxygen be prevented from contacting the staining solution during development of the gel matrix because of the inhibitory effect of oxygen on $LDH_k$. Accordingly, it is preferable to maintain the solution in a nitrogen environment which is insured by bubbling nitrogen gas continuously through the solution throughout the staining process. To reduce the hazard of implosion during the staining process, no vacuum evacuation step is utilized.

Development may be stopped at any time after three hours by soaking the gel in 45% methanol/10% acetic acid (vol/vol) according to customary procedures. It should be noted that the developing reaction will continue for approximately 16 hours but ceases to develop at a constant linear rate after about 8 hours. Accordingly, a constant time span preferably between 3-8 hours should be utilized for all samples assayed to allow for meaningful comparisons.

In order to calibrate the gel one lane is reacted with a known standard such as an aliquot of purified rat $LDH_k$.

Based upon this improved staining process it has now become possible to quantitatively determine the activity levels of serum $LDH_k$ which are associated with primary cancer and metastatic cancer. The following Example illustrates the usefulness of serum $LDH_k$ levels as a serum marker, and is not intended to limit the scope of this invention.

EXAMPLE

MATERIALS AND METHODS (a) Preparation of Serum Samples

Human cancer patient and donor control serum samples were obtained from the Blood Bank at Roswell Park Memorial Institute, buffalo, N.Y. The whole blood samples were allowed to coagulate and spun at 1500 r/min for ten minutes in a Beckman centrifuge (Model TJ-6) to separate the contents into a blood cell clot layer and a serum layer. All samples were stored at 4° C. for immediate use, and aliquots stored at −70° C. for future assay.

The cancer patient samples were removed from the blood cell clots within a few hours after being drawn from the patients, and were up to two to three weeks old when obtained for analysis. Healthy control samples were removed from the clots within a few hours after extraction, and analyzed within one to four days. This second control group was also analyzed again three weeks later to ensure that a three week storage period had no effect of the isozyme levels in the patient samples.

Routinely, 20 μl of 50% sucrose containing 0.01% bromophenol blue was mixed with each sample prior to electrophoresis to render the sample more dense and to facilitate gel loading.

(b) Classical LDH isozyme analysis

All isozyme analyses were done using non-denaturing slab gel electrophoresis systems. A Bio Rad Model 220 dual vertical slab gel electrophoresis cell (Hoefer Scientific) was used for the electrophoretic procedures. To quantitate the classical standard muscle (M) and heart (H) isozymes of LDH, a modification of the procedure of Dietz and Lubrano [Anal. Biochem. 20, 246-257 (1967)] was used. Since the M and H isozymes migrate towards the anode, a normal polarity gel system is utilized. The gels were cast using a Tris-HCl buffer made of of 3.76M Tris which is lowered to a pH of 8.9 using concentrated HCl. A Tris/gylcine buffer (pH 8.3) composed of 0.05M Tris and 0.38M glycine was used for the upper and lower reservoir electrophoresis buffers. The 3 mm thick, 20 well, 5.5% polyacrylamide slab gels were run at 4° C. for three hours at a current of 40 MA per gel. Cooling was provided by circulating ice water.

After the three hour run, the gels were stained specifically for LDH activity by the nitroblue tetrazolium/phenazine methosulfate procedure of Dietz and Lubrano. In this procedure the staining mixture was composed of 0.1M lithium lactate, 1.0 mM NAD+, 0.023 mg/ml of phenazine methosulfate, 0.40 mg/ml nitroblue tetrazolium, and 0.10M Tris-HCl buffer, pH 7.5. Staining was done in the dark for 30 minutes at room temperature.

Following the staining procedure, gels were fixed in 45% methanol/10% acetic acid (vol/vol), photographed, and then scanned with a tungsten filament recording densitometer (Quick Scan Jr., Helena Laboratories) to quantitate the intensity of the protein bands. The densitometer was set at a gain of seven and speed of ten.

(c) Analysis of $LDH_k$ isozyme

A reverse polarity gel system was used to isolate the $LDH_k$ isozyme which has a positive charge at pH 8.9 and migrates towards the cathode. The gel system was based on an imidazole/borate buffer system. The samples were analyzed on 3 mm thick, 20 well, 5.5% polyacrylamide slab gels photopolymerized with a riboflavin catalyst in the absence of persulfate. The gels were cast with a 0.15M potassium tetraborate buffer at pH 8.3. The lower reservoir buffer was 0.10M potassium tetraborate, pH 8.3, and the upper reservoir buffer contained 0.08M imidazole and 0.02M boric acid, pH 8.9. Gels were run an average of 16 hours at a voltage of 220 V, with cooling provided by circulating ice water.

Staining was done using the nitroblue tetrazolium/phenazine methosulfate composition of Dietz and Lubrano as described previously using 1M Tris buffer, pH 8.0. The staining mixture was supplemented with 2% glycerol to complex with the borate ions. These gels were stained in the dar at a temperature of about 37° C. for 4½ hours in an Ehrlenmeyer suction flask under a nitrogen atmosphere. After staining, the gels were fixed, scanned to measure the amount of stain, and stored as described above.

(d) Gel units

To determine the quantity of production of reduced nicotinamide adenine dinucleotide (NADH) represented by one gel unit, known amounts of nicotinamide adenine dinucleotide ($NADH_2$) were electrophoresed on a Tris/glycine gel, stained for one hour, and scanned as described. The quantities of $NADH_2$ tested were: 10 nM, 30nM and 100nM. The quantity of $NADH_2$ electrophoresed was divided by the number of cycles registered by the densitometer when the activity stained band was scanned. This was done for each quantity of $NADH_2$ tested, and an average value of NADH produced per gel unit (one densitometer cycle) was calculated.

This determination was made because clinical laboratory LDH values are expressed in international units (IU) per liter. One IU is equivalent to the production of 1μmol/min NADH.

(e) Staining kinetics

To observe the rate of the reaction catalyzed by $LDH_k$, a staining kinetics experiment was conducted. Two different patient serum samples were electrophoresed using the imidazole/borate system and stained for two, four, six and eight hours each. This was done to ensure that band intensity is a linear function of quantity of $LDH_k$ present and that the assay was not saturated.

(f) Patient serum $LDH_k$ dose response

An experiment was done to determine the relationship between volume of patient serum loaded onto the gel and intensity of the $LDH_k$ activity band seen after staining. Volumes of 10, 30, 60, 80 and 100μ l of serum from a patient with an extremely elevated level of serum $LDH_k$ were electrophoresed, activity stained and scanned according to the procedure described in (c) above.

(g) Inhibition of serum $LHD_k$

An inhibition experiment was conducted on the serum $LDH_k$. Samples were loaded onto a 1.5 mm, 10 well imidazole/borate gel and run for the usual 16 hours at 220 V. At the completion of the run, the gel lanes were sliced apart and stained for 4½ hours in the staining mixture of step (c) under an oxygen or a nitrogen atmosphere, or under an oxygen atmosphere in the presence or absence of 5mM NaCN, $3\times10^{-5}$M adenosine tetraphosphate ($AP_4$), or $3\times10^{-5}$M diadenosine tetraphosphate ($AP_4A$). Gels were then fixed, scanned and stored as described above.

(h) Sample protein concentration

Calculation of the serum sample protein concentration was performed using prior known methods. The optical density of a sample was measured at 180 nm and 260 nm and the ratio of $A_{280}/A_{260}$ was calculated. Protein concentration was then calculated using a conversion factor obtained from a table in *Data For Biochemical Research*, Dawson, R. M. C. et al. (2nd Ed. 1969). The equation for calculation of sample protein concentration is as follows: Protein concentration (mg/ml)=$A_{280}\times$conversion factor$\times 1/d$, where d=length of light path in cm.

(i) Patient information

All of the data regarding the patients utilized in this study were obtained from patient charts through the Medical Records Office at Roswell Park Memorial Institute. The following information was recorded for each patient: age, sex, disease and stage, regions of metastases, all periods and modes of treatment (including surgery, radiation, immunotherapy, and chemotherapy) and clinical laboratory LDH values.

The serum $LDH_k$ values of all patients were categorized according to the presence of absence of metastatic disease. Patients were also divided into four major treatment categories as follows: No surgery within the past year and no other therapy (i.e., chemotherapy, radiation treatment) within the past month; no surgery in the past year, but some other form of therapy in the past month; surgery in the past year, but no other therapy in the past month; and surgery in the past year along with other treatment within the past month.

SUMMARY OF RESULTS (a) Characteristics of the assay for $LDH_k$

As described more fully below, an $LDH_k$-like activity was detected in the serum of many cancer patients. The enzyme activity observed in the electrophoretic assay was proportional to the amount of serum added down to about 5 $LDH_k$ units. Below this point, the assay was nonlinear in a way which tended to diminish differences among weakly positive sera.

This $LDH_k$ activity was unchanged after three weeks' storage at 4° C., and it was also unchanged after a cycle of freezing and thawing.

(b) $LDH_k$ in serum of cancer patients and healthy controls

FIG. 1 presents the $LDH_k$ activity found in the serum of 206 cancer patients and 30 healthy donors. The data are separated according to disease site or type of neoplastic disease and each symbol represents the serum $LDH_k$ activity for one patient. Those patients with known metastatic disease are indicated by filled symbols. Many of the cancer patients had elevated serum $LDH_k$, compared to the control group. The value 2 units per 0.1 ml can serve as a division between normal levels and elevated levels, being two standard deviations above the mean for the control group. About half of the cancer patients have serum $LDH_k$ above this level.

Figure 2:
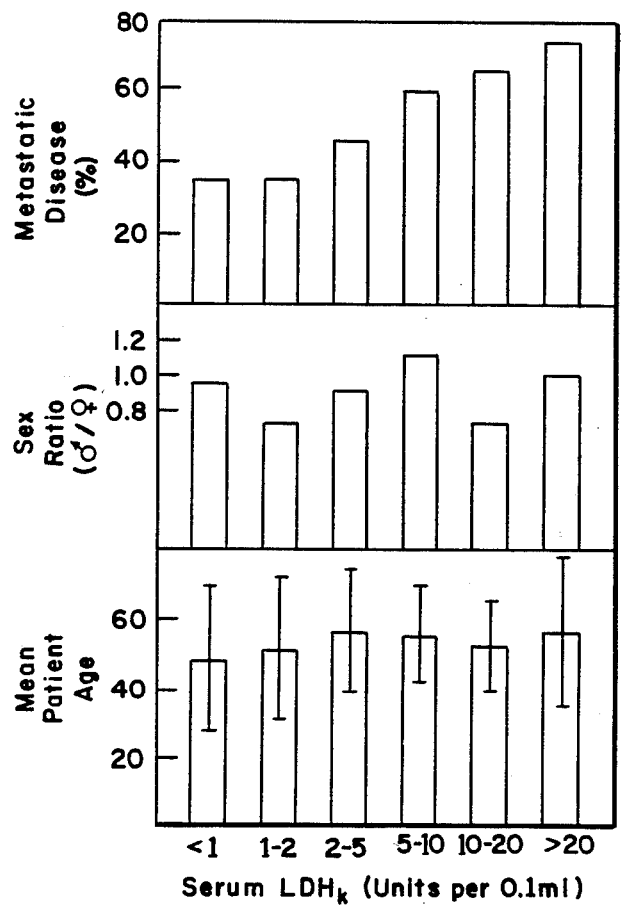
FIG. 2 shows the correlation between serum $LDH_k$ and metastasis.

In general, there seems to be a correlation between serum $LDH_k$ and the presence of metastatic disease. 54% of the patients with serum $LDH_k$ above 2 had metastatic disease, while 35% of those with serum $LDH_k$ below 2 did so. In the following disease groups, all of the patients with serum $LDH_k$ above the disease group mean had metastatic tumors: colon, breast, uterus, kidney, liver, pancreas, and melanoma. The correlation between serum $LDH_k$ and metastasis is presented again in FIG. 2, in which three parameters are compared to serum $LDH_k$ levels. For this chart, the data in FIG. 1 have been grouped into six serum $LDH_k$ classes. Mean age values were based on data available for 66% of the total patients studied. For the upper two sections of the drawing figure, the number of patients in each group was 63, 52, 61, 25, 12 and 8; for the lowest section, they were 36, 33, 47, 17, 10 and 4. There is an evident correlation with presence of metastatic disease, but none with patient age or sex.

Figure 3:
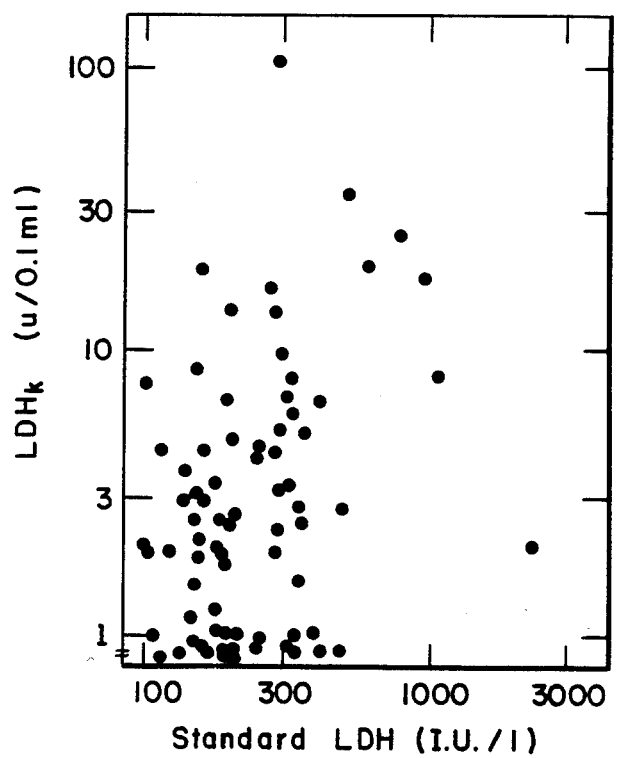
FIG. 3 shows a comparison of serum $LDH_k$ and clinical serum LDH activity.

Standard LDH isozymes are also sometimes elevated in the sera of patients with neoplastic disease. However, as shown in FIG. 3, wherein each point represents one patient of the 114 patients in the eight major disease classes of FIG. 1, there is little or no correlation between standard LDH activity and $LDH_k$ activity. This is consistent with previous work which has shown that $LDH_k$ differs from the classical isozymes both biochemically and in its expression during the cell cycle.

(c) Serum $LDH_k$ in sera of 80 patients with nonmalignant disease

The control sera in FIG. 1 were from healthy donors. Although exact age data on them was not available, it was known that they were younger, as a group, than the cancer patients. To examine serum $LDH_k$ in patients with nonmalignant disease, we obtained sera from Buffalo General Hospital, assayed them for $LDH_k$, and then consulted the hospital records for diagnostic information. The patients whose diagnosis did not include cancer are summarized in Table 3:

TABLE 3

| Diagnosis | Sex/Age | $LDH_k$ units per 0.1 ml |
|---|---|---|
| Diabetes, arteriosclerotic heart disease, anemia, small bowel obstruction (cancer not ruled out) | F/81 | 26 |
| Cholangitis, perforation of gall bladder | F/70 | 17 |
| Back pain | F/73 | 14 |
| Lumbar disc protrusion | M/31 | 12 |
| Leg ulcers, bed sores | F/90 | 11 |
| Cataract | F/65 | 11 |
| Phlebitis of leg | F/73 | 11 |
| Diabetes, hypergastrinemia | | 10 |
| Anteroseptal myocardial infarction, left ventricular aneurysm, coronary artery disease | M/40 | 10 |
| Coronary spasm, mitral valve prolapse, colecystitis | F/60 | 8 |
| Right tympanoplasty | F/52 | 7 |
| Common duct cyst | F/71 | 6 |
| Inflammatory perirectal cyst | F/56 | 6 |
| Coronary artery disease | M/65 | 4 |
| Nine patients | | 3 |
| Fifty-seven patients | | <2 |

Patients whose diagnosis indicated cancer were omitted from the Table. There were 11 such patients; 7 had serum $LDH_k$ greater than 2 units, 4 had 2 units or less. Of 78 patients, 13 (17%) had values greater than 3 units and 22 (28%) had values greater than 2. This group may still include patients who have cancer; in many cases the diagnostic work was either incomplete or unavailable. As a result, it was not possible to exclude the possibility of malignant disease from the patients included in Table 3.

The mean age of the 13 non-cancer patients with $LDH_k$ greater than 3 was 64. This was higher than the mean age of the non-cancer patients with 3 units $LDH_k$ (49 yr) and it was also higher than the mean ages of any of the groups of cancer patients shown in FIG. 2. However, the differences are not statistically significant.

(d) Electrophoretic variants of serum $LDH_k$

In a few cases, electrophoretic variants of serum $LDH_k$ were apparently detected. A section of one electropherogram contained three of these, all of which migrated less rapidly than the usual form of serum $LDH_k$. The patients with these apparent variants had different types of tumors—colon, pharyngeal and testicular. The serum enzyme in all but these three cased comigrated with tumor $LDH_k$; samples of these three tumors were not available to assay for variant $LDH_k$.

(e) Inhibition by diadenosine tetraphosphate

One unusual characteristic of $LDH_k$ is that its activity is inhibited by diadenosine tetraphosphate and diguanosine tetraphosphate. The Ki for these inhibitors is about 50 micromolar, and they are not competitive with $NAD^+$. This property is shared by $LDH_k'$ from cells transformed by Ki-MSV, from human tumors, from human liver, and from rat retina. In contrast, human serum $LDH_k$ is not inhibited by diadenosine tetraphosphate. This property may reflect a unique source for the serum enzyme or it may reflect modification of the enzyme by serum components.

DISCUSSION

As shown by FIG. 1, many of the cancer patients tested had elevated serum $LDH_k$, compared to the control group. The value 2 units per 0.1 ml can serve as a division between normal levels and elevated levels, being two standard deviations above the mean for the control group. About half of the cancer patients had serum $LDH_k$ above this level. This observation does not necessarily imply that metastatic disease produces serum $LDH_k$. It may be that the types of tumor which tend to be metastatic in the population tested also tend to be $LDH_k$-producing.

It also appears that different types of malignant disease may vary in the occurrence of serum $LDH_k$. Among the 23 disease groups presented in FIG. 1, 8 had samples from at least ten patients. These groups were colon, breast, ovarian, lung, oral and pharyngeal, melanoma, Hodgkins's disease and malignant lymphoma, and actue myelccytic leukemia. Of these groups, colon tumor patients had the highest mean serum $LDH_k$ and oral and phryngeal tumor patients had the lowest. The difference between these two groups was significant.

Serum $LDH_k$ may also appear in patients with non-malignant diesease. The interpretation of the data on this point is somewhat limited by the fact that only partial diagnostic information was available from some patients. That is, some patients may have had undocumented malignant disease. Further researach is needed to define the nonmalignant conditions which cause the appearance of serum $LDH_k$ and to establish the origin of serum $LDH_k$ in such patients.

The source of the serum $LDH_k$ in the patients tested has not yet been determined. Since many tumors contain high levels of $LDH_k$, it is reasonable to assume that they may secrete it or release it during necrosis of parts of the tumor. On the other hand, since anoxia is known to induce $LDH_k$ in rat cells and rat muscle, it is possible that $LDH_k$ is produced in nontumor tissue as a result of circulatory disturbance caused by the tumor mass. It may also be released by some other tissue as a more indirect effect of cancer.

In general, there is a correlation between serum $LDK_k$ and the presence of metastatic disease. 54% of the patients with serum $LDH_k$ above 2 had metastatic disease, while 35% of those with serum $LDH_k$ below 2 did so. In the following disease groups, all of the patients with serum $LDH_k$ above the disease group mean had metastatic tumors: colon, breast, uterus, kidney, liver, pancreas, and melanoma.

Figure 4:
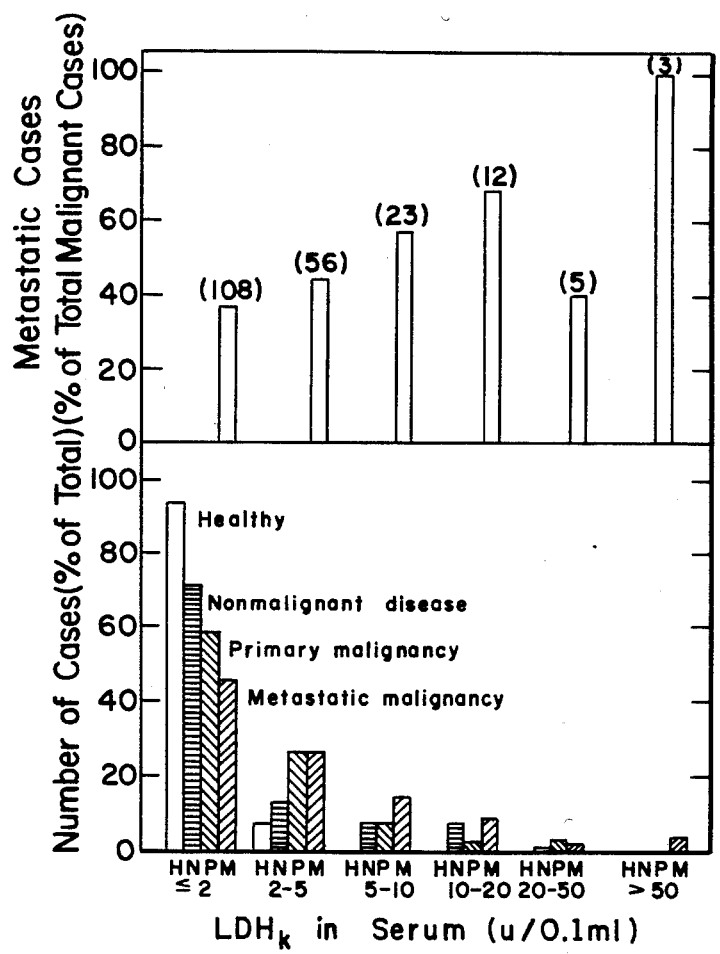
FIG. 4 further illustrates the correlation between serum $LDH_k$ and metastasis.

The correlation between serum $LDH_k$ and metastases is presented further in FIG. 4. For this figure, patients were grouped according to the activity of $LDH_k$ in their serum. The upper part of FIG. 4 shows that the patients with high serum $LDH_k$ were predominantly those with metastatic cancer. The lower part of FIG. 4 compares the data on patients with malignant disease (from FIG. 1) with that from 85 patients with nonmalignant disease. Patients with malignancy tend to be in the higher serum $LDH_k$ groups, and the highest values are found in patients with metastatic malignancy. The upper part of FIG. 4 shows the proportion of malignant cases which are metastatic for each serum $LDH_k$ group. Again, metastatic cases tend to be found among cases with high serum $LDH_k$ activity.

Figure 5:
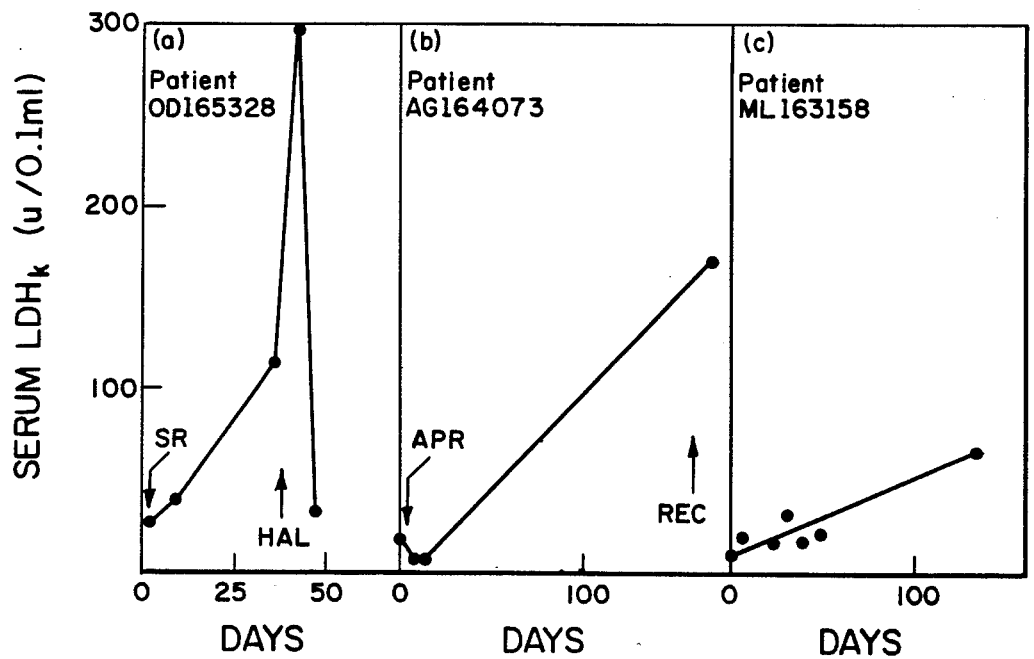
FIG. 5 presents data for three patients having metastatic colorectal cancer over a period of time.

FIG. 5 presents data for three patients having metastatic colorectal cancer over a longer period of time. FIG. 5a presents a patient who had liver metastatses involving 40% of the liver at the time of surgery to remove the primary tumor (SR). Over the next month, his serum $LDH_k$, already high, rose about four-fold. He was then given a hepatic artery ligation (HAL), at which time has liver metstases were seen to involve 60% of the liver. These was a temporary rise in serum $LDH_k$ after the ligation, and then it dropped to what it had been at the time of this first surgery. This course suggests that serum $LDH_k$ was an indicator of the extent of metastases in this patient.

FIG. 5b presents a patient who had no evidence of metastases at the time of surgery to remove her primary tumor (APR). Five months later she returned with a greatly elevated serum $LDH_k$ and extensive peritoneal, liver and lung metastases.

FIG. 5c presents data for a patient whose primary tumor had been removed but who had bony metastases in the sternum. These metastases progressed during the time period shown, and the serum $LDH_k$ level rose. This patient may also have had liver metastases, but this possibility could not be documented.

Based upon the above results it has now been determined that many, but not all, people with cancer have $LDH_k$ at relatively high levels in their serum. This means that a large population including those with undiagnosed cancer could be screened for serum $LDH_k$. Of those members of the population exhibiting an elevated serum level of 2 units or greater, it would be possible to identify slightly over half of those individuals having cancer. In other words, a positive assay would be a very good indication that cancer was present, although a negative assay would still not exclude the possibility of cancer. As a result, $LDH_k$ activity cannot be used by itself to diagnose the presence of primary cancer without recourse to other clinical and laboratory data.

However, the above results further show that patients with metastatic cancer have a much higher probability of expressing serum $LDH_k$ than patients with primary cancer. This capability of detecting metastatic cancer is of great significance, as such secondary tumors are typically far more lethal than primary tumors. Consequently, it has been shown that serum $LDH_k$ is particularly useful as a maker to aid in the determination of whether metastatic cancer has recurred following treatment of a primary tumor, and also as a guide in monitoring the success or failure of further therapy.

Accordingly, it is further contemplated as within the scope of this invention to assemble the essential components of this assay process into a kit suitable for use in laboratories. As stated above, knowledge of $LDH_k$ levels are significant in the diagnosis of primary and secondary cancer. Commerical laboratories, hospitals and clinics would have a substantial need for such an assay kit. This need could be best supplied by having available the necessary reagents for gels and staining mixtures needed to complete the assay arranged within a suitable portable container or kit together with appropriate instructions concerning the assay and staining procedures. It is recognized that as of the present time the particular components of the gels required for $LDH_k$ separation by electrophoresis are not commercially available, and that the preparation of the gels as utilized in the electrolytic separation process described herein is as yet too complex to be carried out in other than well equipped commercial or industrial laboratories. However, it is foreseeable that at some future time the reagents described herein will be commercially available and that the electrophoretic separation process and equipment required for $LDH_k$ separation may be improved sufficiently to permit operation in less sophisticated laboratory facilities. Presumably, a kit containing the staining reagents described herein either in bulk or in premeasured packaging, along with suitable instructions for stain development could then be made readily available by commercial distribution to all laboratories, clinics and hospitals.

We claim:

1. In a known process for quantitatively detecting $LDH_k$ isozyme in human serum utilizing reverse polarity electrophoresis on an imidazole/borate buffered polyacrylamide gel matrix according to known techniques, followed by staining the gel matrix using standard nitroblue tetrazolium/phenazine methasulfate or an equivalent staining solution, the improvement comprising continuously contacting said gel matrix with said staining solution having a constant temperature between 30°–40° C. for at least 3 hours in the absence of both oxygen and light to provide a suitable stain reaction time.

2. The improved process according to claim 1 wherein said gel is submerged within the staining solution.

3. The improved process according to claim 2 wherein the pH of the staining solution is maintained between 7.8–9.0 during said reaction time.

4. The improved process according to claim 3 wherein the temperature of the staining solution is maintained at about 37° C. during said reaction time.

5. The improved process according to claim 4 wherein the pH of the staining solution is about 8.0 during said reaction time.

6. The improved process according to claim 5 wherein the staining solution used during said reaction time has a pH of about 8.0 and a temperature of about 37° C.

7. The improved process according to claim 6 wherein said reaction time is between 3–8 hours.

8. The improved process according to claim 7 wherein said reaction time is at least 4.5 hours.

9. The improved process according to claim 8 wherein said staining process is performed in a nitrogen environment.

10. A method for determining in a patient the presence or absence of cancer which comprises extracting from said patient a sample of blood, and measuring the quantitative relative activity level of $LDH_k$ isozyme present within the serum of said sample by the method of claim 1 and comparing said level to the level of $LDH_k$ measured in the serum of an individual free of cancer.

11. The method of claim 10 wherein the patient's level of $LDH_k$ is compared with a standard curve showing average nomal or base line levels of serum $LDH_k$ activity.

12. The method of claim 11 wherein the $LDH_k$ activity is determined in said patient's serum after the patient has undergone treatment for cancer and compared with the level of $LDH_k$ activity in the serum of an individual free of cancer to determine whether metastasis has occurred after therapy.

13. The method of claim 12 wherein the $LDH_k$ activity level is determined in said patient's serum after the patient has undergone treatment for cancer and compared with the level of $LDH_k$ activity in the serum of an individual free of cancer to monitor cancer treatment response.

14. A method using $LDH_k$ isozyme as a serum marker for detecting the presence of cancer in a patient wherein the serum level of the patient's $LDH_k$ is determined by the method of claim 1.

15. A diagnostic test kit for performing the method of claim 1 comprising:
(a) a given quantity of a suitable electrophoresis matrix for use in electrophoretically separating $LDH_k$ isozyme;
(b) A given quantity of a borate buffer having a concentration greater than or equal to 10mM borate ion for treating the serum prior to or simultaneously with electrophoresis;
(c) a given amount of appropriate staining reagents for the colorimetric determination of $LDH_k$;
(d) means for excluding light and oxygen from the testing environment;
(e) a positive control comprising an aliquot of purified $LDH_k$;
(f) directions for the performance of said method; and
(g) a container for housing the materials present in steps (a)–(f).

* * * * *